(12) United States Patent
Blancher et al.

(10) Patent No.: US 10,821,150 B2
(45) Date of Patent: Nov. 3, 2020

(54) INFANT NUTRITION FOR IMPROVEMENT IN INSULIN SENSITIVITY LATER IN LIFE

(71) Applicant: NESTEC S.A., Vevey (CH)

(72) Inventors: Florence Blancher, Morges (CH); Catherine Mace, Lausanne (CH); Yassaman Shahkhalili Dulloo, La Tour de Peilz (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/100,427

(22) PCT Filed: Nov. 27, 2014

(86) PCT No.: PCT/EP2014/075831
§ 371 (c)(1),
(2) Date: May 31, 2016

(87) PCT Pub. No.: WO2015/078974
PCT Pub. Date: Jun. 4, 2015

(65) Prior Publication Data
US 2016/0296585 A1     Oct. 13, 2016

(30) Foreign Application Priority Data
Nov. 29, 2013   (EP) .................... 13195014

(51) Int. Cl.
| A61K 38/01 | (2006.01) |
| A23L 33/00 | (2016.01) |
| A23L 33/19 | (2016.01) |
| A61K 9/00 | (2006.01) |

(52) U.S. Cl.
CPC ............ *A61K 38/018* (2013.01); *A23L 33/19* (2016.08); *A23L 33/40* (2016.08); *A61K 9/0056* (2013.01)

(58) Field of Classification Search
None
See application file for complete search history.

(56) References Cited

FOREIGN PATENT DOCUMENTS

| EP | 1932437 A1 * | 6/2008 |
| EP | 2583562 | 4/2013 |
| WO | 02083164 | 10/2002 |
| WO | 2008054192 | 5/2008 |
| WO | 2010027258 A1 | 3/2010 |
| WO | 2010112429 | 10/2010 |
| WO | 2010112430 | 10/2010 |
| WO | 2010119088 | 10/2010 |
| WO | 2013109367 | 7/2013 |

OTHER PUBLICATIONS

MayoClinic—Diabetes risk factors, copyright 1998-2017—accessed Aug. 3, 2017.*
Gillies et al. (BMJ, doi:10.1136/bmj.39063.689375.55, published Jan. 19, 2007).*
Web MD—Metformin oral—copyright 1998-2017, accessed Aug. 3, 2017.*
Enteral nutrition formulary guide (<https://kr.ihc.com/ext/Dcmnt?ncid=520448890> Nov. 25, 2008).*
Virginia WIC eligible formulas (<http://www.vdh.virginia.gov/content/uploads/sites/43/2017/02/Formulary.pdf>2017).*
Centers for Disease Control and Prevention (<https://www.cdc.gov/nutrition/infantandtoddlernutrition/formula-feeding/how-much-how-often.html> May 7, 2018).*
Koletzko et al. ("Lower protein infant formula is associated with lower weight up to age 2 y: a randomized clinical trial" Am J Clin Nutr 2009:89:1836-45).*
Obesity Prevention Source (<https://www.hsph.harvard.edu/obesity-prevention-source/obesity-causes/prenatal-postnatal-obesity/>Mar. 18, 2011).*
Deglaire et al. ("Hydrolyzed dietary casein as compared with the intact protein reduces postprandial peripheral, but not whole-body, uptake of nitrogen in humans"; Ann J Clin Nutr 2009:90:1011-22).*
Stengel et al. "High-protein diet selectively reduces fat mass and improves glucose tolerance in Western-type diet-induced obese rats" Am J Physiol Regul Integr Comp Physiol, 2013, vol. 305, pp. R582-R591.
Coleman et al. "Effect of Diet on Incidence of Diabetes in Nonobese Diabetic Mice" Diabetes, 1990, vol. 39, pp. 432-436, XP001002589.
Fairweather et al. "Type 1 diabetes: virus infection or autoimmune disease?" Nature Immunology, Apr. 2002, vol. 3, No. 4, pp. 338-340.
Virtanen et al. "Cow's Milk Consumption, Disease-Associated Autoantibodies and Type 1 Diabetes Mellitus: a Follow-up Study in Siblings of Diabetic Children" Diabetic Medicine, 1998, vol. 15, pp. 730-738.
Paronen et al., "Effect of Cow's Milk Exposure and Maternal Type 1 Diabetes on Cellular and Humoral Immunization to Dietary Insulin in Infants at Genetic Risk for Type 1 Diabetes", vol. 49, Issue No. 10, Oct. 2000, pp. 1657-1665.
Australian Office Action for corresponding Australian Application No. 2014356452, dated Oct. 3, 2018; (5 pages).

* cited by examiner

*Primary Examiner* — James H. Alstrum-Acevedo
*Assistant Examiner* — Tara L Martinez
(74) *Attorney, Agent, or Firm* — K&L Gates LLP

(57) ABSTRACT

The present invention relates to a nutritional composition for use in treatment, prevention and/or reducing the risk of a metabolic syndrome disorder appearing later in life, wherein the nutritional composition comprises casein.

15 Claims, 10 Drawing Sheets

Figure 3
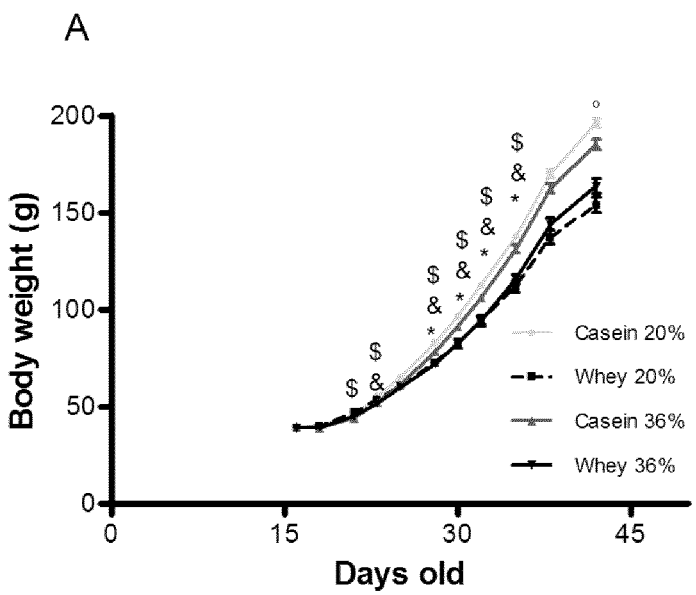
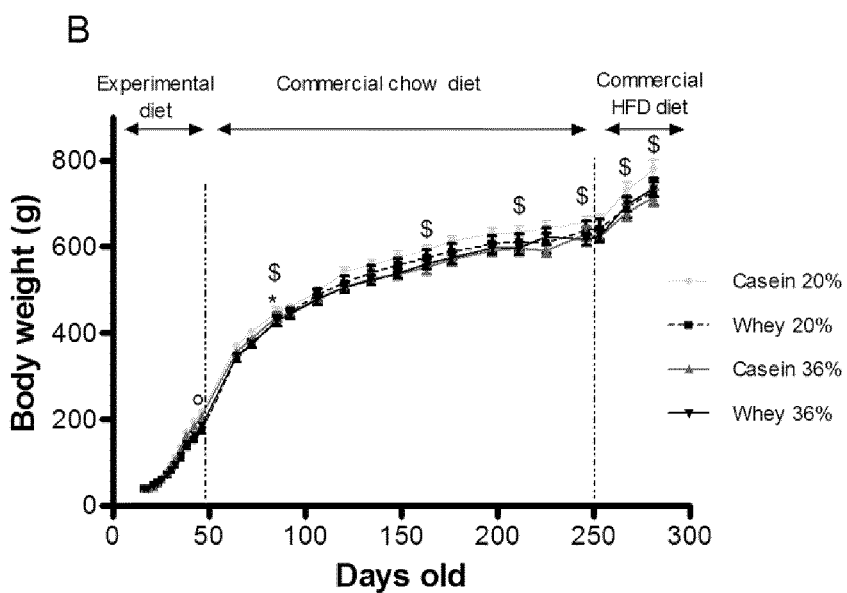

Figure 5
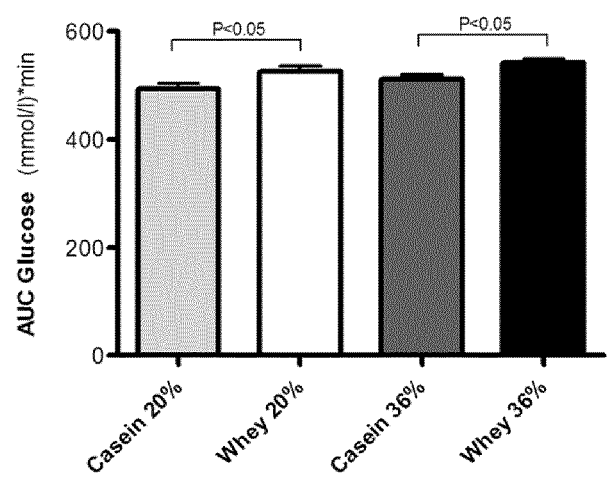
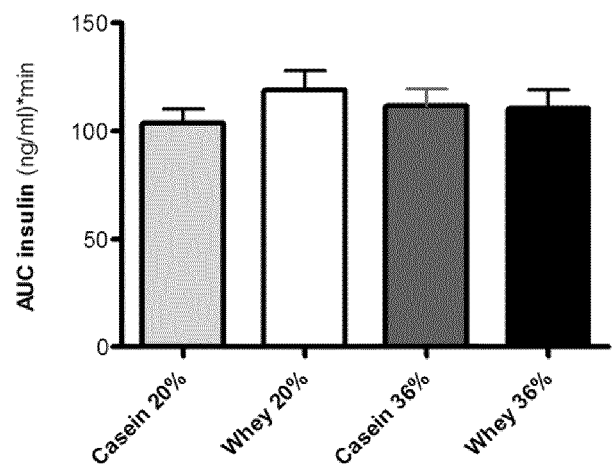

Figure 7 A- C
A
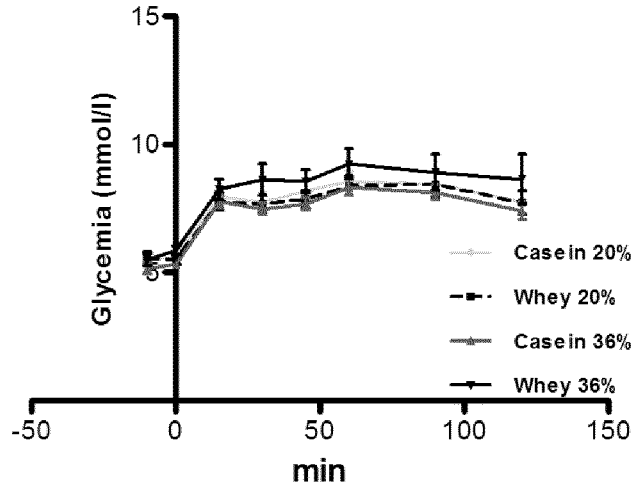
B
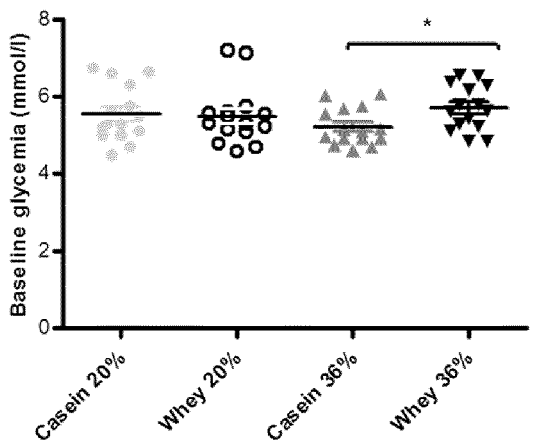
C
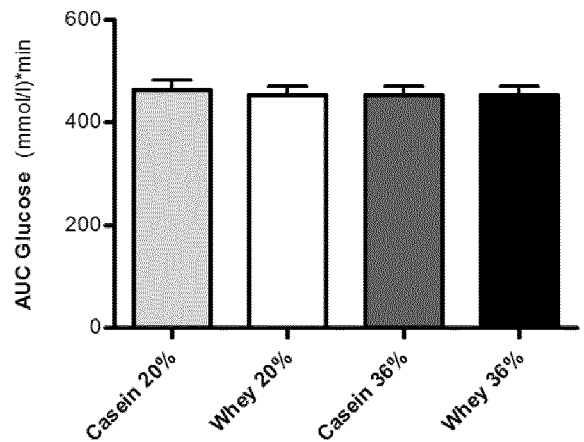

Figure 7 D- F
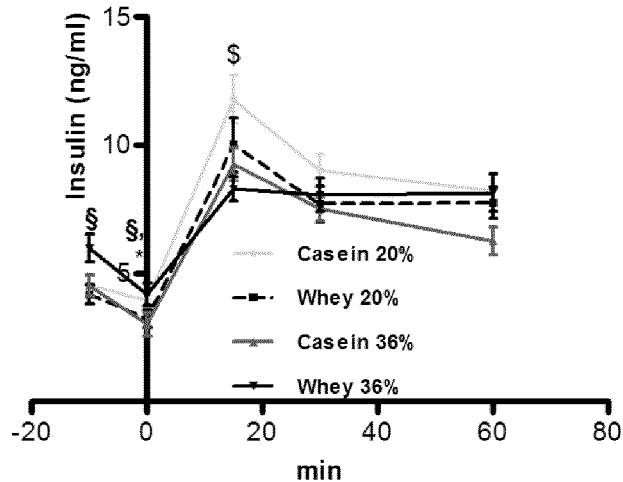
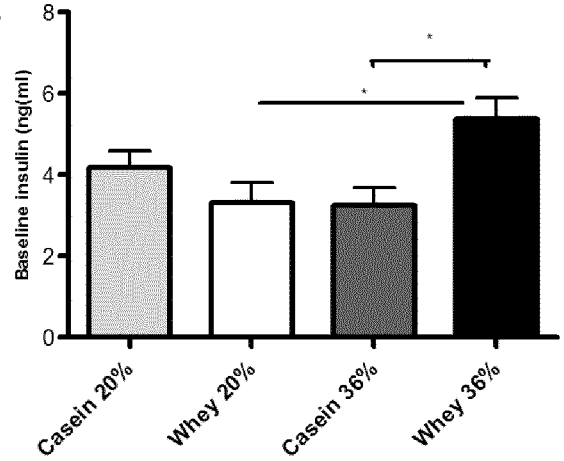
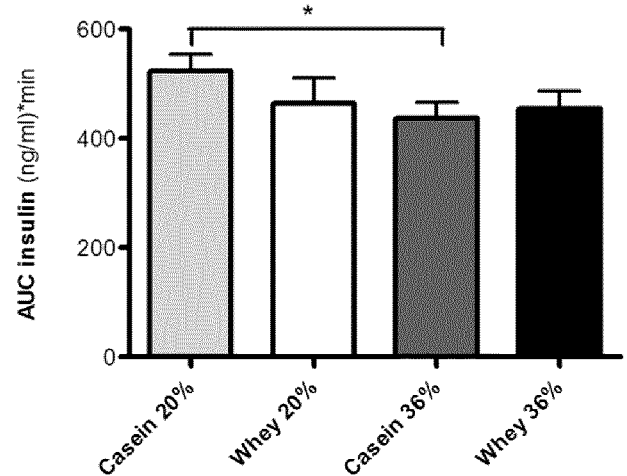

Figure 8
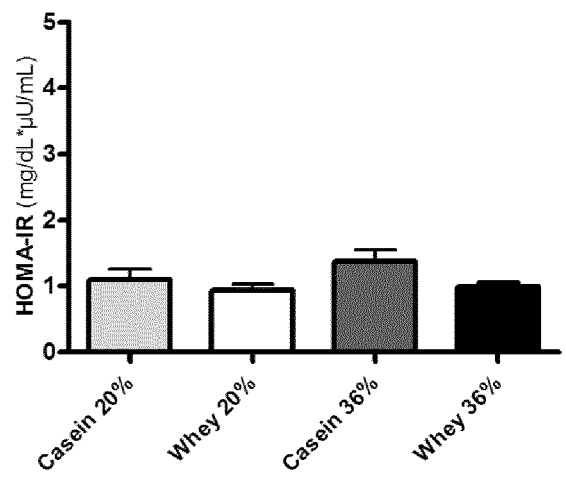
A
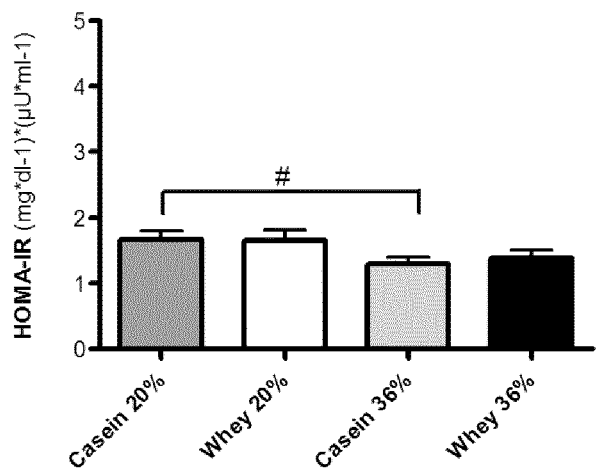
B
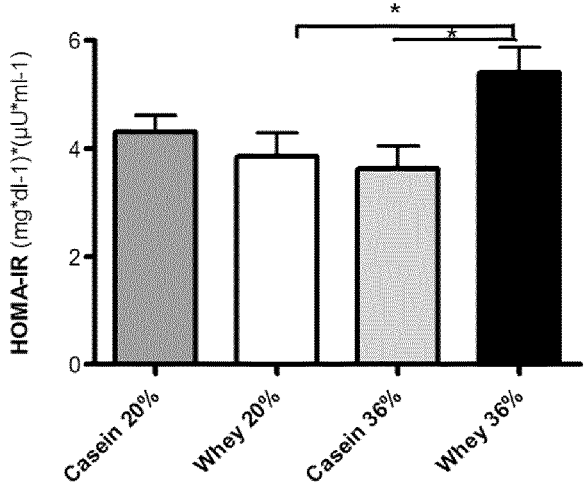
C

INFANT NUTRITION FOR IMPROVEMENT IN INSULIN SENSITIVITY LATER IN LIFE

CROSS REFERENCE TO RELATED APPLICATIONS

The present application is a National Stage of International Application No. PCT/EP2014/075831, filed on Nov. 27, 2014, which claims priority to European Patent Application No. 13195014.9, filed Nov. 29, 2013, the entire contents of which are being incorporated herein by reference.

TECHNICAL FIELD OF THE INVENTION

The present invention relates to a nutritional composition for use in, prevention and/or reducing the risk of a metabolic syndrome disorder, wherein the nutritional composition comprises casein.

BACKGROUND OF THE INVENTION

It is now well recognized that suboptimal nutrition during critical periods of development may induce long-term alterations in organ structures or functions, which can predispose humans to later chronic diseases (1-5). This concept known as an early programming is strongly supported by several large epidemiological and clinical studies indicating an association between markers of early nutrition (size at birth, size in infancy, rate of early growth) and risk for later adult hypertension, diabetes, coronary heart disease and obesity (4; 6; 7).

Thus, the prenatal and early postnatal periods are now recognized as critical windows for early programming, with interest focused upon the size at birth (2;7;8), breast feeding and its duration; (9-13), kinetics of early growth (6;14-16), and more recently on the protein content of infant formula (17).

Given that prenatal and early postnatal nutrition plays a role in determining susceptibility to develop one or more metabolic syndrome disorders later in life, there is clearly a need for intervention at these stages which will reduce the risk for developing disorders later in life.

Hence, a nutritional composition for administration early in life which reduces the risk for development of metabolic syndrome disorders later in life would be advantageous.

There is a particular need to specific nutritional compositions that may be administered at particular intervention windows during the early life of the infants and which may be capable to reduce the risk, prevent, or reduce the severity of sub-optimal health conditions usually associated with metabolic syndromes, such as over-weight, obesity, diabetes or even cardiovascular diseases.

There is an even particular need in these infants at higher risk to develop such sub-optimal conditions, for example because of their genetic heritage, of the health conditions of their parents, of their difficult early development.

SUMMARY OF THE INVENTION

The present inventors have surprisingly shown that rats which were fed a diet with casein protein as pups, experience a protective effect on insulin sensitivity when they were exposed to an adipogenic diet as adult rats. In contrast, rats which had been fed a diet with whey protein as pups were not protected when exposed to an adipogenic diet as adults. Instead, the rats which had been fed whey-based diet as pups, displayed impaired insulin sensitivity, indicated by an increased HOMA-IR.

HOMA-IR (homeostatic model assessment of insulin resistance) is a method used to quantify insulin resistance and beta-cell function. It was first described under the name HOMA by Matthews et al. in 1985 (Diabetologia 28 (7): 412-9). An increased HOMA-IR is indicative of increased insulin resistance/reduced insulin sensitivity.

It has previously been presented (WO2010/112430) that compositions comprising bovine casein proteins (relative to whey) improves insulin sensitivity in the specific cases of low birth weight, and in normal birth weight which experience accelerated growth (catch up growth), following energy restriction. However, the long-term consequence of early protein intake on insulin sensitivity under normal conditions of adequate birth weight and normal growth—without food restriction and in the absence of catch-up growth—was not known.

The present inventors have surprisingly shown that the feeding of casein early in life can improve glucose tolerance in short-term and improve insulin sensitivity in long-term, later in life. This is especially apparent when subjects are challenged with adipogenic diet in adult age, later in life.

This is surprising because the conditions of the subjects in the previous study are known to already show symptoms of decreased insulin sensitivity. However, the present study shows that even in the absence of any negative factors, the insulin sensitivity of the subject can be improved. Furthermore, improvement can be seen even later in life.

Accordingly, a first aspect of the present invention relates to a nutritional composition for use in treatment, prevention and/or reducing the risk of a metabolic syndrome disorder later in life, wherein a) the composition comprises more than 70 weight % casein based on the total protein content of the composition, and b) the composition is to be administered to the infant or young child from birth up to 36 months of age.

In one embodiment of the this aspect, the invention relates a nutritional composition for use in treatment, prevention and/or reducing the risk of a metabolic syndrome disorder later in life, wherein a) the composition comprises more than 70 weight % casein based on the total protein content of the composition, and b) the composition is to be administered to the infant or young child from birth up to 36 months of age, and wherein the total protein content of the nutritional composition is at least 0.5 g protein/100 kcal.

Another aspect of the present invention relates to the use of casein for the preparation of a nutritional composition for use in treatment, prevention or reducing the risk of a metabolic syndrome disorder later in life in an individual, wherein: a) the composition comprises more than 70 weight % casein based on the total protein content of the composition, and b) the composition is to be administered to the infant from birth up to 36 months.

The invention also provides a method of treating, preventing, and/or reducing the risk that an infant or child will develop a metabolic syndrome disorder later in life; in particular when challenged with adipogenic diet, said method comprising the step of administering a nutritional composition comprising more than 70 weight % casein based on the total protein content of the composition.

BRIEF DESCRIPTION OF THE FIGURES

FIG. 3 shows Body weight during the experimental diet (Phase I) (A) and body weight throughout the study (B) Data are presented as med±SEMed. $ Significant difference between Casein 20 E % and Casein 36 E %; & significant difference between Casein 20 E % and Whey 20 E %; * significant difference between Whey 36 E % and Casein 36 E %. ° All groups are different.

FIG. 7 shows Oral glucose tolerance test at the end of the study ie at the end of Phase II:B(287 days old). Glycemic response to a glucose load (A);Baseline glycemia (B); Area under the glucose curve (C); Insulin response to a glucose load (D); Baseline insulinemia (E); Area under the insulin curve (F). Results are expressed as med±SEMedian. $ significant difference (P<0.05) between Casein 20 E % and Casein 36 E %;*significant difference (P<0.05) between Whey 36 E % and Casein 36 E %; § significant difference (P<0.05) between Whey 20 E % and Whey 36 E %;*significant difference at P<0.05.

FIG. 8 shows the HOMA-IR levels throughout the study. At the end of the experimental diet (Phase I, 42 days old) (A); During the phase II on chow diet (Phase II: A, 165 days old) (B); At the end of the study on HFD (high fat diet) (Phase ILB, 287 days old) (C).Results are expressed as med±SEMedian.* significant difference at P<0.05; # significant difference at P<0.01.

DETAILED DESCRIPTION OF THE INVENTION

Definitions

Figure 1:
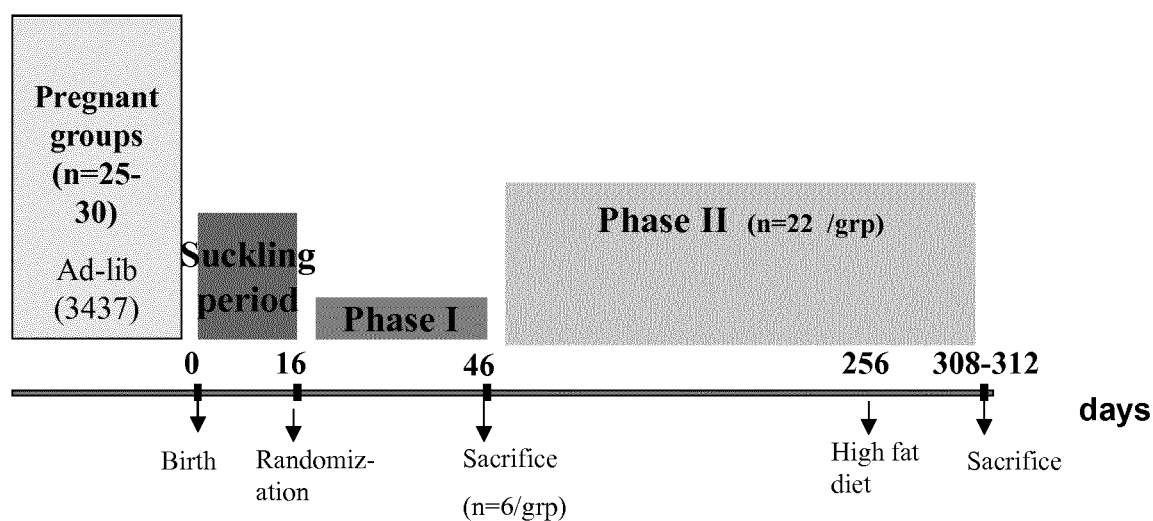
FIG. 1 shows a diagram of the experimental design, including all the interventions.

Prior to discussing the present invention in further details, the following terms and conventions will first be defined:

In the context of the present invention, mentioned percentages are weight/weight percentages unless otherwise stated.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

The term "infant" means a child under the age of 12 months.

The term "young child" means a child older than 12 months and up until 3 years of age.

The term "reducing the risk of" means that the event is less likely to happen compared to the appropriate and usual reference (such as a general population or normal weight infants or young children).

The term "prevention" means that the event or disorder is prevented from taking place either completely, or partially (i.e., a milder form occurs and/or occurs later). The term prevention also comprises a reduction in the severity of the event or disorder (or health condition) or a reduction in the frequency of occurrence of such events or disorders or a delaying effect on such events or disorders.

The terms "normal weight/overweight/underweight" refer to the internationally recognized tables for weight of infants, young children and children, and are in particular function of the age of the subject.

Composition for Use

The invention in a first aspect relates to a nutritional composition for use in treatment, prevention and/or reducing the risk of a metabolic syndrome disorder later in life, wherein a) the composition comprises more than 70 weight % casein based on the total protein content of the composition, and b) the composition is to be administered to the infant or young child from birth up to 36 months of age.

Casein as used in the present application refers to the family of related proteins found in mammalian milk.

The casein may be from any suitable source or combination of sources of mammalian milk. Examples of sources include, for example, cow, goat, buffalo, sheep etc. One embodiment relates to a composition for use according to the invention wherein the casein is bovine. Bovine casein is readily available commercially.

The nutritional composition according to the invention comprises more than 70% weight casein based on the total protein content of the composition. Thus the invention in one embodiment relates to a nutritional composition according to the invention wherein composition comprises for example at least 75 weight %, at least 80 weight %, at least 85 weight %, at least 90 weight %, at least 95 weight %, at least 99 weight %, about 100 weight % casein based on the total protein content of the composition.

In other embodiments, the nutritional composition comprises at least 85 weight % casein based on the total protein content of the composition, such as at least 90%, for example at least 95 weight %, at least 99 weight %, or for example 100 weight % of casein based on the total protein content of the composition.

In a further embodiment, 100% of the protein present in a nutritional composition for use according to the invention is casein.

The total protein content of nutritional composition according to the invention may be for example at least 5 g/l, for example at least 6 g/l, for example at least 7 g/l, such as at least 8 g/l, for example at least 9 g/l, such as at least 10 g/l, at least 11 g/l, for example at least 12 g/l, such as at least 15 g/l, or for example 18 g/l; or may be for example about 9 or about 10 g/l.

In other examples, the total protein content of nutritional composition for use according to the invention may be from 3 g/l to 33 g/l ready to consume composition, such as from 3 g/l to 25 g/l, for example 5 to 20 g/l, for example 8 to 20 g/l.

The total protein content of a nutritional composition according to the invention, in particular infant formulas, may be required by a food authority to meet certain specifications regarding amount of protein.

In examples of nutritional compositions which are intended for infants, the total protein content may be for example from 3 g/l to 15 g/l of ready to consume formula, such as 5 to 15 g/l, such as 3 to 10 g/l.

The total protein content may also be expressed as g protein per kcal of nutritional composition.

Thus, where the nutritional composition of the invention is a nutritional composition for infants, such as for example an infant formula, the total amount of protein may be for example at most 5 g/100 kcal of ready to consume formula, for example from 1 to 4 g/100 kcal, such as from 1 to 3.5 g/100 kcal, such as from 1.5 to 2.5 g/100 kcal, such as from 1.6 to 2.2 g/100 kcal. One specific embodiment relates to a nutritional composition for use according to the invention, wherein the total protein content is 1.8 g/100 kcal of ready to consume formula.

A further specific embodiment of the present invention relates to an infant formula wherein the total protein content is from 1.6 to 2.2 g/100 kcal, such as 1.8 g/100 kcal, and wherein more than 70% of the total protein content is from casein A still further embodiment of the embodiment of the present invention relates to an infant formula wherein the casein content is at least 0.45 g casein/100 kcal of ready to consume formula.

Nutritional compositions of the invention which are intended for young children may have the same protein content as nutritional compositions which are intended for infants, or may comprise higher or lower levels of protein.

For example, a nutritional composition for young children may comprise lower total protein content, for example 0.5 to 5 g/100 kcal, such as from 0.5 to 3.5 g/100 kcal, such as from 1 to 2.5 g/100 kcal; or for example from 0.5 to 1.5 g/100 kcal total protein content.

Protein

The proteins may be intact or hydrolysed or a mixture of intact and hydrolysed proteins. The hydrolysed proteins can be fully hydrolysed or partially hydrolysed.

The nutritional composition of the invention comprises more than 70% casein based on the total protein content of the composition The remainder of the protein content may comprise one or more protein suitable for consumption by infants or young children provided that the minimum requirements for essential amino acid content are met.

For example, the total protein content of the composition may consist of a mixture of casein and whey proteins, such as a mix of bovine casein and bovine whey proteins. If whey proteins are to be used, they may be acid whey or sweet whey or mixtures thereof and may include alpha-lactalbumin and beta-lactoglobulin in whatever proportions are desired. The protein source may additionally be supplemented with free amino acids if this is necessary to meet the minimum requirements for essential amino acid content. These requirements are published for example in EC Directive 2006/14 I/EC.

In other examples, the total protein content of the composition may consist of casein and one or more non-dairy proteins, for example selected from the group consisting of meat, fish, egg, and/or vegetarian protein sources such as pea, rice and the like.

The ratio of casein to the remainder of the protein content may be from 70:30 to 100:0 (casein:remainder of protein). Examples of ratios are 70:30, 80:20, 85:15, 90:10, 95:5, 100:0 (casein:remainder of protein).

As noted above, the protein source may be a mixture of casein and whey proteins. The whey protein may be a whey protein isolate, acid whey, sweet whey or sweet whey from which the caseino-glycomacropeptide has been removed (modified sweet whey). Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. A process for removing CGMP from sweet whey is described in EP 880902.

If modified sweet whey is used as the whey protein in a mixture of 60% whey and 40% casein, the protein source may be supplemented by free tryptophan, isoleucine, histidine and phenylalanine in amounts of up to 0.34% for tryptophan, 0.92% for isoleucine, 0.19% for histidine and 2.2% for phenylalanine (in each case as a percentage by weight of total protein content). If intact sweet whey is used as the whey protein in a mixture of 60% whey and 40% casein, the protein source may be supplemented by free tryptophan, leucine, histidine and phenylalanine in amounts of up to 0.5% for tryptophan, 0.37% for leucine, 0.3% for histidine and 2.5% for phenylalanine (in each case as a percentage by weight of total protein content). The protein source may also be supplemented by amino acids rich in sulphur such as cysteine and methionine if desired.

Composition for Use—Disorders

The inventors have shown that adult rats which were fed a diet where casein was predominant protein source as pups, display an improved HOMA-IR index when challenged with an adipogenic diet as adults, as compared to rats which were fed a diet where whey was predominant source of protein as pups.

Thus, the invention relates to a nutritional composition for use in treatment, prevention and/or reducing the risk of a metabolic syndrome disorder later in life, wherein a) the composition comprises more than 70 weight % casein based on the total protein content of the composition, and b) the composition is to be administered to the infant or young child from birth up to 36 months of age.

The term "metabolic syndrome disorder" as used herein refers to one or more disorders associated with Metabolic Syndrome. These disorders are typically a result of a dysregulation of the glucose homeostasis. Examples of such disorders include diabetes such as diabetes mellitus, impaired glucose tolerance, impaired fasting glucose, insulin resistance, hypertension, dyslipidemia, overweight, obesity (particularly central obesity) and microalbuminuria.

Thus the invention relates in one embodiment to the composition for use according to the invention wherein the disorder is selected from the group consisting of diabetes mellitus, impaired glucose tolerance, impaired fasting glucose, insulin resistance, hypertension, dyslipidemia, overweight, obesity (particularly central obesity) and microalbuminuria.

In other embodiments, the invention relates to the composition for use according to the invention, wherein the use is to improve insulin sensitivity, to promote normal weight and/or to prevent overweight later in life.

Without wishing to be bound by theory, it is thought that the early diet leads to a programming, which in turn gives a protective effect which is apparent later in life, and in particular when challenged with an adipogenic diet later in life.

Thus, the present invention relates to a nutritional composition for use in treatment, prevention and/or reducing the risk of a metabolic syndrome disorder later in life.

The term "later in life" in the context of the present invention refers to the period of time after childhood, that is after 12 years of age. In embodiments of the invention, the metabolic syndrome disorder appears after 12 years of age, or for example after 15 years of age, such as after 18 years of age, such as after 25 years of age, after 30 years of age, after 35 years of age.

The experimental data shows that when adult rats where challenged with a high fat (i.e., adipogenic) diet, adults who had been fed casein 36 E % diet as pups displayed a lower HOMO-IR (indicative of a better insulin sensitivity), as compared to those adults which had been fed a whey 36 E % diet as pups.

Accordingly, a further embodiment of the invention relates to a composition for use according to the invention wherein the use is in treatment, prevention and/or reducing the risk of a metabolic syndrome disorder appearing later in life when exposed to an adipogenic diet.

The term "adipogenic diet" in the context of the present invention relates to a diet which will lead to increased fat mass of the individual. Generally speaking, an excess of energy intake will lead to increased fat mass, therefore one example of a adipogenic diet is a diet where the caloric intake exceeds the individual's required caloric need. Other examples of an adipogenic diet include the typical Western diet, also known as the western pattern diet or Standard American Diet. Another example of an adipogenic diet is where the diet is characterized by a fat content that exceeds the dietary recommendation of 30% of the energy from fat, high sugar diet and/or that wherein the caloric intake exceeds the individual's required caloric need.

Thus, it is envisaged that the composition for use according to the invention, when administered early in life (for example to an infant or young child), will protect that individual if and when said individual later in life (for example as an adult, or for example after 18, after 20, after 25, after 30 years of age) eats a diet which is adipogenic. By protect, it is meant that glucose homeostasis and/or insulin sensitivity will not be impaired, or will be not be impaired to same extent. Without being bound by the theory, it is hypothesised that the use of the composition of the invention, at the time of administration, modulates the metabolic pathways. Such modulation enables a specific metabolic reaction when the subject is exposed to an adipogenic diet later in life. Such modulation may affect all subjects exposed to the composition of the invention and may not be dependent of whether the subjects have expressed particular metabolic signals of "stressed immediate nutritional needs". For example such modulation may differ from the immediate modulation in subjects having already generated metabolic signals at time of administration of the composition (such as subjects undergoing a catch-up growth or low birth weight infants; i.e infant in stressed immediate nutritional needs). When stressed nutritional signals are present at time of administration, specific metabolic pathways are activated in order to respond to the stress signals. In the context of the invention some other metabolic pathways are activated and induce the long term effect, especially when exposed to a adipogenic diet later in life.

It was also observed that casein diet results in better glucose tolerance at the short term (See FIGS. 8 A, B and C).

Thus, in one aspect, the present invention relates to a nutritional composition for use in treatment, prevention and/or reducing the risk of a metabolic syndrome disorder, wherein a) the composition comprises more than 70 weight % casein based on the total protein content of the composition, and b) the composition is to be administered to a infant or young child from birth up to 36 months of age.

In other embodiments, the invention relates to the composition for use according to the invention, wherein the use is to improve insulin sensitivity, to promote normal weight and/or to prevent overweight.

Composition for Use—Target Groups

The composition for use according to the invention is to be administered to an infant or young child.

In one embodiment the infant or young child is for example born to a mother who herself suffered or suffers from one or more metabolic syndrome disorders, such as one or more selected from the group consisting of diabetes mellitus, impaired glucose tolerance, impaired fasting glucose, insulin resistance, hypertension, dyslipidemia, overweight, obesity (particularly central obesity) and microalbuminuria, or from gestational diabetes.

In a further embodiment the infant or young child is deemed to be at risk for one or more metabolic syndrome disorders, for example due to a familial risk, such as family history.

In one embodiment, the composition for use is to be administered to an infant or young child, regardless of birth weight.

In another embodiment of the present invention, the composition for use according to the invention is to be administered to an infant or young child whose birth weight was normal. In another embodiment the birth weight of the infant or young child was above normal.

In a further embodiment, the present invention relates to a composition for use according to the invention, wherein the composition is to be administered to an infant or young child who has not undergone a period of catch-up growth following a period of growth restriction.

In yet a further embodiment, the present invention relates to a composition for use according to the invention, wherein the composition is to be administered to infant or young child who was born with normal birth weight and with a non restricted food intake and normal growth during infancy and/or young age.

Dosage Regimen

The invention relates to the surprising finding that administration of casein based nutritional compositions to an infant or young child can protect from metabolic syndrome disorders later in life.

The composition for use according to the invention is to be administered to the infant or young child in a time period from birth to 36 months. In other embodiments, the administration falls in a time period from birth to 36 months, or 24 months, such as to 18 months, for example to 12 months.

In one embodiment of the present invention, the composition for use according to the invention is administered to an infant or young child during the weaning period.

The weaning period refers to the period in an infant's or young child's life where they are transitioned from milk feeding (such as breast milk feeding) to solid foods. This period depends on the individual infant or young child, but typically falls within the range from 4 months to 18 months of age, such as from 6 to 18 months.

In one embodiment of the present invention, the composition for use according to the invention is administered to an infant or young child during the weaning period and not before (i.e. starting at the weaning period). In one embodiment the administration starts shortly before the weaning period (for example 1 month before the start of the weaning).

In this time period (which may according to the above be for example the weaning period, or from birth to 36 months, birth to 24 months, birth to 18 months, or birth to 12 months), administration may be for example intermittent during said period, or for example on average once daily over said the period, or for example once every other day over said period, or for example at least once daily during said period.

In another embodiment of the present invention, the administration of the composition is for a shorter duration of time falling within the time period mentioned above, for example on average once daily for a duration of at least six weeks in said time period; such as for example on average once daily for 3, 6, 8, 9 months during said time period.

Alternatively, the administration may be for example on average once every other day for a period of at least six weeks in the period from birth to 36 months, such as for example on average once every other day for a period of 3, 6, 8, or 9 months during said time period.

In other embodiments the invention relates to a use according to the invention, wherein a composition is administered at least once a day for at least 1 month.

Nutritional Composition Formats

A medical food is a special class of nutritional composition designed to provide dietary management of certain conditions. The medical food meets certain criteria as set out by and regulated under the Orphan Drug Act of 1983 in Section 5 [360ee](b)(2)(D). The medical food may be presented in any suitable format, as discussed below.

Thus, one embodiment of the invention relates to a nutritional composition according to the invention wherein the nutritional composition is a medical food.

The nutritional composition according to the invention may be in any suitable format.

The format of the nutritional composition for use according to the invention may be tailored to suit the age of the infant or young child to whom it is administered.

Examples of nutritional composition formats suitable for infants include an infant formula, a follow-on formula, a growing up milk, a human milk fortifier. The infant formula may be for example a nutritionally complete formula.

Examples of formats suitable for infants and/or young children include ready-to-drink compositions, liquid comestibles, milk drinks, milk-shakes, milk-biscuits, yoghurts, soups, desserts, puddings, bars such as cereal bars, porridges, beverages and baby foods.

In preferred embodiments, the format of the nutritional composition is a dairy-based format, such as for example milk and milk drinks, milk-shakes, milk biscuits, yoghurts and other cultured milk products, ice creams and cheeses.

Further nutritional composition formats include products comprising dairy products, for example, baked products, dairy products, desserts, confectionery products, cereal bars, breakfast cereals.

Infant Formula

In one preferred embodiment the nutritional composition for use according to the invention is an infant formula.

In infant formula for use according to the invention may comprise, besides the protein source as discussed previously above, also a carbohydrate source and a lipid source.

Any carbohydrate source conventionally found in infant formulas such as lactose, saccharose, maltodextrin, starch and mixtures thereof may be used although the preferred source of carbohydrates is lactose. Preferably, the carbohydrate content of the infant formula is between 9 and 14 g/100 kcal.

An infant formula for use according to the present invention may further contain a source of lipids. The lipid source may be any lipid or fat which is suitable for use in infant formulas. Suitable fat sources include palm olein, high oleic sunflower oil, linseed oil and high oleic safflower oil although a combination of linseed oil and high oleic safflower oil is preferred. Small amounts of oils containing high quantities of preformed arachidonic acid (ARA) and docosahexaenoic acid (DHA) such as fish oils or microbial oils may be included. In total, the lipid content may be between 4.4 and 6 g/100 kcal. Preferably, the ratio of linoleic acid (C18:2n-6): [alpha]-linolenic acid (C18:3n-3) in the lipid source is less than 7:1, more preferably between 7:1 and 5:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B 1, vitamin B2, vitamin B6, vitamin B 12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population. If necessary, the infant formula may contain emulsifiers and stabilisers such as soy lecithin, citric acid esters of mono- and di-glycerides, and the like.

The infant formula may optionally contain other substances which may have a beneficial effect such as probiotic lactic acid bacteria, prebiotic oligosaccharides, lactoferrin, nucleotides, nucleosides, and the like.

The formula may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenized; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. or about 85° C.; for example by flash cooling. The liquid mixture may then be again homogenized; for example in two stages at about 10 MPa to about 30 MPa in the first stage and about 2 MPa to about 10 MPa in the second stage. The homogenized mixture may then be further cooled to add any heat sensitive components; such as vitamins and minerals. The pH and solids content of the homogenized mixture are conveniently adjusted at this point.

The homogenized mixture is transferred to a suitable drying apparatus such as a spray drier or freeze drier and converted to powder. The powder should have a moisture content of less than about 5% by weight. If a liquid product is preferred, the homogenized mixture may be sterilized then aseptically filled into suitable containers or may be first filled into the containers and then retorted.

Method of Treatment

The invention in a further aspect relates to a method of treatment, prevention and/or reducing the risk of a metabolic syndrome disorder, in particular insulin resistance, said method comprising administering to an infant or young child a nutritional composition according to the invention.

Combination of Disclosures

It should be noted that embodiments and features described in the context of one of the aspects of the present invention also apply to the other aspects of the invention.

The compositions for use according to the invention are herein described by different parameters, such as the ingredients, nutritional composition formats, uses, target groups etc. It should be noted that embodiments and features described in the context of one of the parameters of the composition for use according to the invention, may also be combined with other embodiments and features described in the context of another parameter, unless expressly stated otherwise.

All patent and non-patent references cited in the present application, are hereby incorporated by reference in their entirety.

The invention will now be described in further details in the following non-limiting examples.

EXAMPLES

Methodology and Trials

See FIG. 1 for an overview of the experimental design.

The following abbreviations are used: D=day(s); H=hour(s), g=gram(s),

TABLE 1

| | Study design | | | |
|---|---|---|---|---|
| | Gestation period | Suckling period | Phase I | Phase II |
| Diet | Kilba 3437 | Kilba 3437 | Experimental diet | D46-D255: Kilba 3437 D256-D269 Kilba 2126 |
| Food intake + spillage measurement | 1/week | 1/week | 5/week Pair-feeding if required | Once a week |
| Body weight measurement | 1/week | None At D16 | 3/week | Once a week |
| NMR | | | D17-18 D37-389 | D105-106 D162-163 D224-225 D252-523 D282-283 |

TABLE 1-continued

| | Study design | | | |
|---|---|---|---|---|
| | Gestation period | Suckling period | Phase I | Phase II |
| GTT | | | D42 to D45 (n = 20/grp) | D164-165: fasting glycemia insulinemia (n = 22) D287-290: GTT (n = 15/grp) |
| D$_2$0 | | | D49-50 (n = 6 rats per group) | D297 to 298 (n = 7 rats per group) |

D = days

Coupling Conditions and Gestation Period

Programmed mated Sprague-dawley rats (SD, n=38) of 10-11 weeks old with following characterization were purchased from Charles River (France). Female virgin SD rats with close body weight of 250±30 g, were single coupled during their estrus cycle with male SD rats, characterized by a homogenized body weight and age (371±11 g, 9-11 weeks old). The coupling exposure was limited to only 20 hr. Thirty eight animals with expelled vaginal plugs were selected and send to NRC on post mating day of 3.

Upon arrival, the female rats were caged individually and feed ad-libitum with a laboratory chow diet (kliba 3437) until birth.

Suckling Period

At birth, only dams and their pups bearing at least 8 pups with minimum 3-4 males per litter, were included in the study. The number of pups in each litter was limited to 8, with preference to male pups. All dams were fed ad-libitum with a rat chow diet (Kliba 3437) during the lactation period. The pups remained with their mother until age of 16 days (2 days after eye opening). During this period, they were allowed to suckle ad-libitum from dams.

Weaning Period (Phase I)

Pups were separated from dams and the same number of male pups from each litter (sibling) were randomly allocated into one of the following four study groups based on their body weight.

a) Casein 20 E % group (Casein 20 E %)
b) Whey 20 E % group (Whey 20 E %)
c) Casein 36 E % group (Casein 36 E %)
d) Whey 36 E % group (Whey 36 E %)

Pups were fed with one of the following experimental diet different in type of protein (casein or whey) or level of protein (20 E % or 36 E % protein). from age of 16 d until 45 d of age. The diets were isonitrogenous at same level of protein and isoenergetic in all groups. The extra protein in high protein groups (36 E % protein) was exchanged with carbohydrate (corn starch). The composition of experimental diet is shown in in Table 2.

Six pups per group were euthanized at the end of phase I (d42-45) by decapitation as described in below.

TABLE 2

| | Experimental diet composition | | | |
|---|---|---|---|---|
| Products | 20 Casein diet | 20 Whey diet | 36 Casein diet | 36 Whey diet |
| Corn starch | 53 | 53 | 37 | 37 |
| Casein | 20 | — | 36 | — |
| Whey | — | 20 | — | 36 |

TABLE 2-continued

Experimental diet composition

| Products | 20 Casein diet | 20 Whey diet | 36 Casein diet | 36 Whey diet |
|---|---|---|---|---|
| Sucrose | 10 | 10 | 10 | 10 |
| Soybean oil | 7 | 7 | 7 | 7 |
| Cellulose | 5 | 5 | 5 | 5 |
| Mineral mix AIN93G | 3.5 | 3.5 | 3.5 | 3.5 |
| Vitamin mix AIN93 | 1.0 | 1.0 | 1.0 | 1.0 |
| L-cysteine | 0.3 | | 0.3 | |
| Bitartr. choline | 0.25 | 0.25 | 0.25 | 0.25 |
| Tert-butylhydroquinone | 0.014 | 0.014 | 0.014 | 0.014 |
| Total (wet weight) | 100 | 100 | 100 | 100 |
| Kcal/100 g diet (calculated on analysed humidity basis) | 362.0 | 362.0 | 368.2 | 368.2 |
| % Dry Wt of powder (based on ingredient humidity basis) | 93.1 | 92.8 | 94.1 | 94.0 |
| % Dry Wt final pellet (analysis) | 90.8 | 90.7 | 88.5 | 88.4 |
| Kcal/100 g powder (final pellet) | 353.02 | 353.77 | 346.28 | 346.26 |
| % Energy | | | | |
| Protein (basis on nunspeed nitrogen results * 6.38) | 21.2 | 21.7 | 35.3 | 36.0 |
| Protein (from ingredient based on humidity results) | 21.4 | 21.4 | 37.6 | 37.6 |
| CHO | 61.2 | 61.2 | 45.3 | 45.3 |
| Fat | 17.4 | 17.4 | 17.1 | 17.1 |
| % Total energy (protein from nunsped results) | 99.8 | 100.3 | 97.7 | 98.4 |
| % Total enery (protein from ingredient based on humidity results | 100.0 | 100.0 | 100.0 | 100.0 |

Whey: prolacta 90 (lactalis)
Casein: from animal house (protein = dry weight)

Post Weaning Period (or Phase II)

During this period all groups received the same diet. First they were all fed with a commercial chow diet with low fat content (Kilba 3437.13% fat energy) until d 255 and then all groups were challenged with a commercial high fat diet (Kliba 2126, 45% fat energy) until the end of the study (308-311 d of age). The remaining animals were euthanized at d 308-311.

Housing Conditions

Animals of the same group were first caged collectively (5/cage) for few days (D16 to D20-21) and then separated and caged individually until the end of the study. They were kept in the same room at 23±3° C. with 55% relative humidity and a 12 h light/dark cycle during the study.

Measurements and Analysis
Physiological Measurements and Sample Collections

Body weight of pups was recorded three times per week and food intake was measured during all working days from d16 to d45 (phase I). Then, body weight and food intake were measured once per week until the end of the study (phase II).

Body composition was measured by nuclear magnetic resonance (NMR) at 17, 37, 104, 162, 224 and 252d.

After 6 hr fast, blood samples were obtained from puncture of the tail at day 164±1, glucose was measured with a glucometer (Ascensia Elite XL, Dublin, Ireland) and blood was centrifuged for plasma recovery.

An oral glucose tolerance test (OGTT) was performed after 6 hr of day food deprivation (from 7.30 am to 13.30 pm) in 20 offspring per group at age of 42±3 and 287±3 days.

During OGTT two baseline blood samples were taken from the tail vein, with at least 10 minutes interval between sampling (time −10 and 0), followed by an oral gavage of glucose solution (30% wt/v) at dose of 2 g/Kg body weight. Then further blood samples were collected from tail incision at 15, 30, 45, 60, 90 and 120 min after glucose administration. All blood samples were analysed directly for blood glucose level, using Ascensia Elite XL glucometers (Bayer AG, Zurich, Switzerland). The blood samples at all time points also were collected in EDTA coated tubes, plasma was separated and stored as is described below for insulin analyses.

Six pups per group were euthanized at d42-45 by decapitation. Blood samples were collected into tubes containing EDTA. Plasma was separated after 10 minutes centrifugation at 2200 rpm, following blood collection. The plasma samples were kept frozen in dry ice and kept at −80° C. until analysis. Liver, pancreas, gastrocnemius, and adipose fat pads (retroperitoneal, epididymal and subcutaneous) were weighted and immediately frozen. The same procedure was repeated in the remaining animals euthanized at d 308-311.

Hormone and Metabolites Analysis

Plasma insulin was measured by an ELISA method using kits from Crystal Chem. Inc (IL, USA). Plasma triglycerides (TG), free fatty acids, glucose and cholesterol were measured at euthanasia using automated chemistry analyzer (COBAS C111 Roche) with the following kits: triglycerides enzymatic kit (Roche Diagnostics, Rotkreuz, CH), free fatty acids enzymatic kit (Wako Chemicals GmbH, Neuss, De), cholesterol enzymatic kit (Roche Diagnostics, Rotkreuz, CH), IGF-1 (IDS, LTD, UK).

For determination of pancreatic insulin, pancreas was homogenized with an acid-ethanol (solution v/v: 75% ethanol, 1.5% of 37% HCl and 23.5% distilled water) and incubated at −20° C. overnight. The insulin content in the supernatant was measured by an ELISA method using kits from Crystal Chem. Inc (IL, USA).

With the fasting values for glucose and insulin, the homeostasis model assessment of insulin resistance (HOMA-IR) was calculated. This valided index of insulin sensitivity in rats (31) is calculated as:

$$\frac{\text{glucose}\left(\frac{mg}{dl}\right) * \text{insulin}(\mu U/ml)}{2430}$$

RT-PCR

Extraction of mRNA from liver, subcutaneous and retroperitoneal adipose tissue was performed with the Agencourt RNA advanced tissue kit (Beckman Coulter, USA). RNA was quantified with the ND-1000 Spectrophotometer (Nano-Drop Technologies, USA). Reverse transcription was performed using the 1st strand cDNA Synthesis kit for RT-PCR (AMV Roche, Del.). Primers were designed with the software Primer express version 3.30 (Applied Biosystems, USA), 13 actin was used as housekeeping gene.

Statistical Analysis

Two different kind of statistical analyses have been performed according to the nature of the outcome:

For the body weight and body weight gain (longitudinal data), a mixed model has been used in each phase of the study (phase I experimental diet; phase II commercial chow diet; phase II high fat diet). These linear mixed models use group, day, squared-day and the pair-wise interactions of group and day variables as fixed effects and a random day and squared-day effect.

For the other outcome taken at a unique time point (or change score of body composition), a nonparametric approach was developed using two-sided Wilcoxon rank-sum tests.

Pvalues of these tests are reported for all different outcomes.

Results

Phase I refers to the phase of the diet where the experimental diet was fed to the pups. During the second phase, Phase II, all pups received the same diets. In the initial part of phase ii (Phase II:A); the pups were fed a normal commercial diet. In the second part, Phase II: B, the pups were challenged with a High Fat Diet.

Energy Intake

Figure 2:
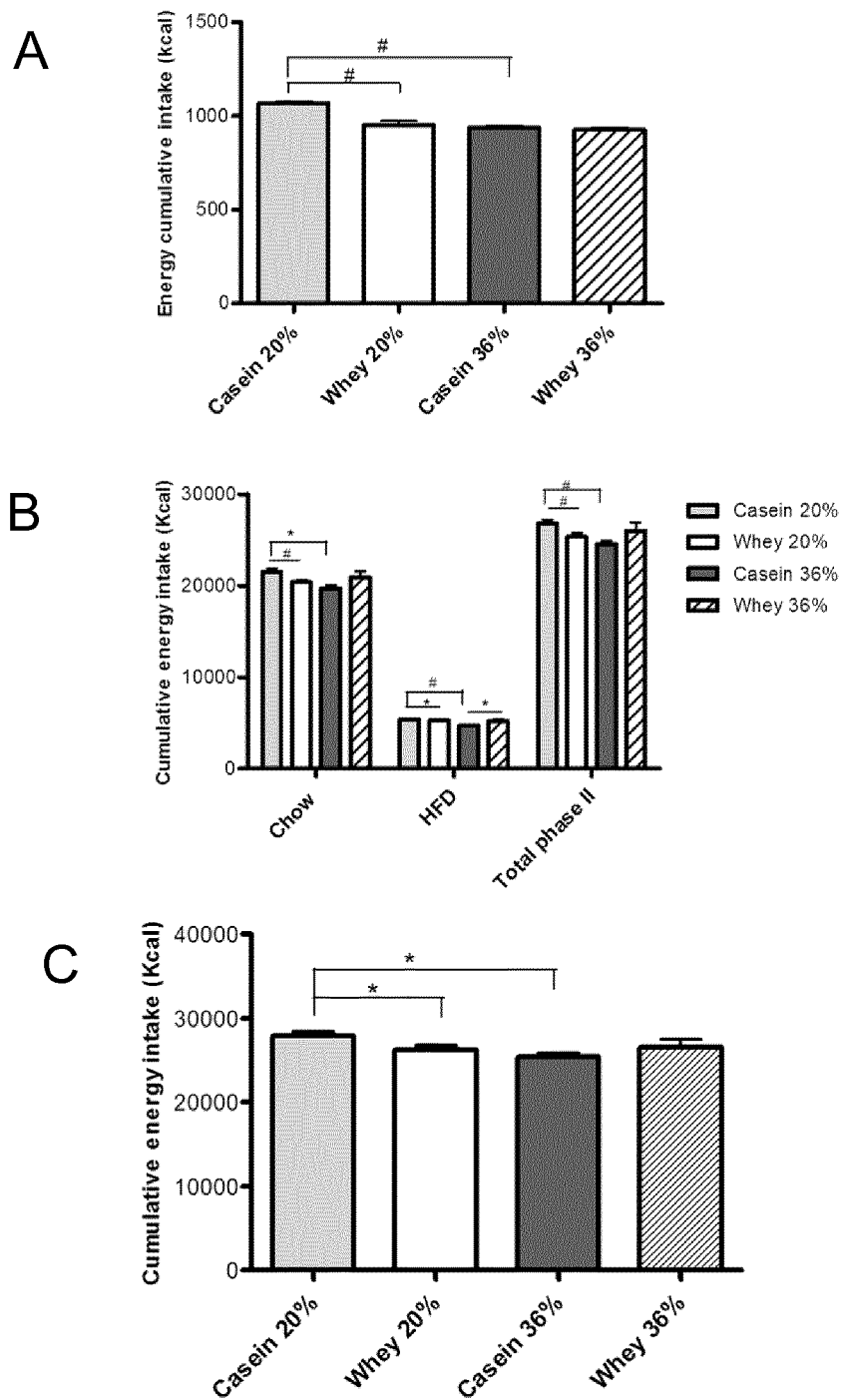
FIG. 2 shows Total energy intake during phase I (A), phase II (B) and whole study (phase I & phase II) (C). Results are expressed as med±SEMedian. * significant difference with P<0.05; # significant difference with P<0.01

FIG. 2 shows the total energy intake.

Casein 20 E % had a significantly higher energy intake than both Whey 20 E % and Casein 36 E % during Phase I (kcal: 1088±12; 982.4±25; 932±12, respectively, P≤0.0001) as well as phase II (when all groups were fed with the same diet), and hence whole study period (phase I+phase II) (p<0.05). Whey 20 E % and Whey 36 E % had similar energy intake during both study phases and hence during whole study period (p>0.05 in all cases).

Casein 36 E % and Whey 36 E % had similar energy intake during phase I. Although Whey 36 E % had higher energy intake than Casein 36 E % during phase II, this difference was only statistically significant during the high fat challenge period (p<0.05) and not entire phase II or whole study period (p>0.05).

Animals fed a low casein diet (Casein 20 E %) after weaning had a significantly higher intake of energy (ate more), compared to animals fed whey 20 E %, Casein 36 E %, and Whey 36 E %, when measured at the end of the Phase I diet.

Body Weight and Weight Gain

Figure 4:
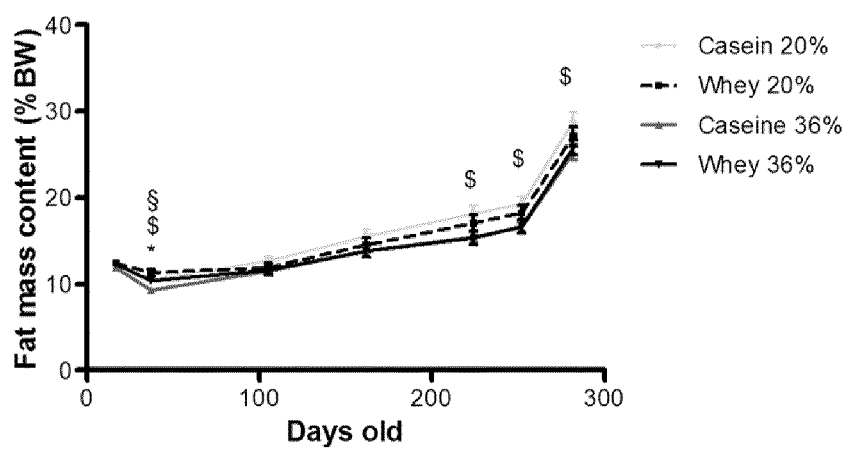
FIG. 4 shows Fat mass content as % BW. Data are represented as median±SEMedian. $ Significant difference (P<0.05) between Casein20 E % and Casein 36 E %; § significant difference (P<0.05) between Whey 20 E % and Whey 36 E %;*significant difference (P<0.05) between Whey 36 E % and Casein 36 E %.
Figure 5:
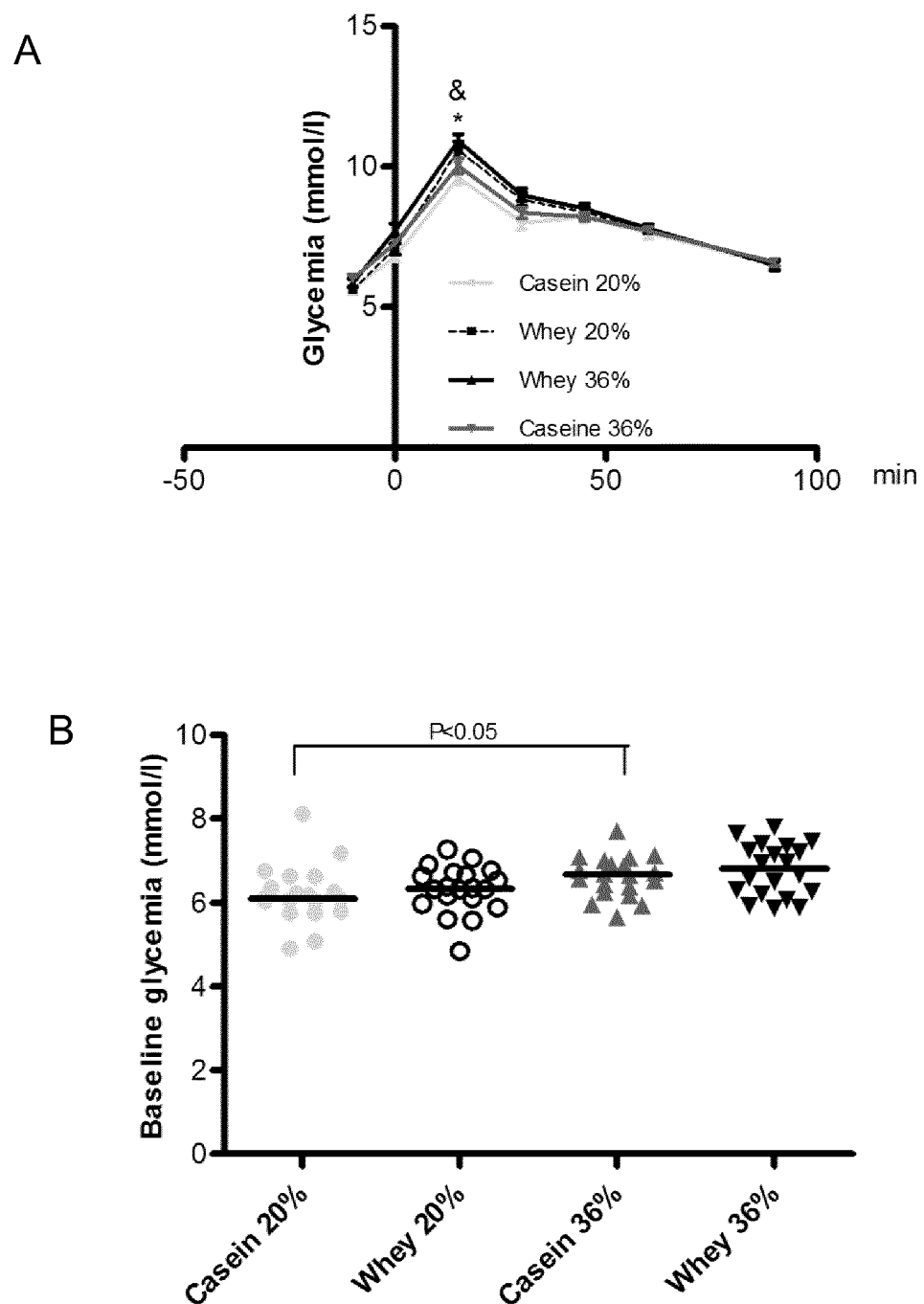
FIG. 5 shows the results of Oral glucose tolerance test measured at the end of the experimental diet (i.e Phase I) (42 days old). (A), Baseline glycemia (B), Area under the glucose curve (C), Area under the insulin curve (D). Results are expressed as med±SEMedian. & significant difference (P<0.05) between Casein 20 E % and Whey 20 E %,*significant difference (P<0.05) between Whey 36 E % and Casein 36 E %.

FIGS. 3 and 4 illustrate the body weight and body weight gain.

During the experimental diet period (Phase I), Casein groups at both levels of protein (20 E % and 36 E %) had a greater weight gain (p<0.0001) than corresponding Whey-fed groups, resulting in a higher body weight (p<0.0001) (See FIG. 3A). At normal protein level (20E %) relative to high level (36 E %), Casein-fed rats had greater weight gain (Casein 20 E %: 156±2.4 g; Casein 36E %: 144±1.6 g; p<0.02) resulting in higher body weight at d42 (Casein 20 E %: 196±2.3 g; Casein 36 E %: 184±2.6 g; p<0.02). In contrary, rats fed with higher whey protein intake (Whey 36 E %) displayed 12% higher weight gain (Whey 20 E %: 113±3.6 g; Whey 36 E %: 127±2.7 g; p=0.001) resulting in 6.5% higher body weight (Whey 20 E %: 153±3.8 g; Whey 36 E %: 163±3.7 g; p=0.05).

During the phase II (FIG. 3B), Casein 20 E % remained heavier than Casein 36 E % while the body weight gain of all 4 groups were similar during the low fat chow diet period. However, during high fat challenge period, Casein 20 E % gained more weight than both of Casein 36 E % and Whey 20 E % (10% and 8% higher, p<0.01 and p<0.05 respectively, FIG. 3B). This was the same for entire duration of study.

Body Composition

The results showed that feeding animals with different quantity and quality of protein in the diet had an impact on the body composition. Indeed, during the experimental diet, both Casein and Whey protein at 36E % resulted in slightly but significant lower % of body fat than at 20E % of protein level (FIG. 4; Casein 20 E %: 10±0.2%; Casein 36 E %: 9±0.3%; Whey 20E %: 11±0.4%; Whey 36: 10±0.3%, p<0.05). Regarding the effect of the quality of protein (Casein vs Whey) during phase I, no difference was observed at 20 E % between the groups, however rats fed Casein diet at 36E % were less fat than those fed Whey 36 E %. These differences disappeared during chow diet feeding but, from later age of 225d until the end of the study, Casein 20E % group became again fatter than Casein 36E % (13% higher % body fat at d283, p=0.01).

Table 3 summarized the changes in body composition. In accordance with the changes in body composition observed, the increase in fat content in Casein 20E % is reflected by a significant higher fat gain relative to Casein 36E % during both phase II & throughout the study (p=0.005 and p<0.01 respectively), resulting in an increase fat/lean mass ratio (obesity index).

TABLE 3

| | Fat gain during different study period | | | | | | | |
|---|---|---|---|---|---|---|---|---|
| | Casein 20 | Whey 20 | Casein 36 | Whey 36 | Casein 20 | Whey 20 | Casein 36 | Whey 36 |
| | During low fat chow diet (46-225 d) | | | | During high fat diet (226-311 d) | | | |
| Fat gain (g) | 108 ± 9 | 90 ± 9 | 90 ± 5$ | 99 ± 8 | 106 ± 7 | 87 ± 9 | 71 ± 5$ | 85 ± 6 |
| | Total phase II | | | | Total Study | | | |
| Fat gain (g) | 221 ± 15 | 171 ± 18 | 156 ± 7$ | 184 ± 12 | 237 ± 14 | 184 ± 19 | 166 ± 7$ | 191 ± 11 |
| % fat change | 19 ± 1.3 | 15.5 ± 1.7 | 14.6 ± 0.8 | 15.9 ± 1.0 | 16 ± 1.5 | 11 ± 1.3 | 12 ± 1.09$ | 13 ± 0.9 |
| Fat/lean ratio | 0.38 ± 0.03$ | 0.28 ± 0.03 | 0.27 ± 0.01 | 0.32 ± 0.02 | 0.35 ± 0.03 | 0.26 ± 0.02 | 0.24 ± 0.02$ | 0.30 ± 0.02 |

Glucose Homeostasis after Phase I

Glucose homeostasis was assessed at different time courses during the study either by performing an oral glucose tolerance test or by measuring fasting value (described above in Materials and Methods).

The experimental diet of Phase I had an effect on the glucose tolerance, as is illustrated in FIG. 8. At the end of phase I, whey-fed groups presented both a higher AUC glucose (p<0.05) and higher Cmax glucose values (p<0.05) relative to casein-fed groups, suggesting a lower glucose tolerance in response to whey diet. Also, Casein 36 E % had a higher fasting glycemia than Casein 20 E % (respectively; 6.7±0.14 and 6.1±0.15 mmol/l, p<0.05).

When animals were fed glucose, Whey-fed groups showed a significantly higher blood glucose peak in response to the glucose feeding, and also a significant increase in the AUC glucose. This shows that they were less able to clear the glucose than those animals fed a casein diet (FIG. 8A), indicating a lower glucose tolerance.

Casein 20 E % had lower baseline glycemia than Casein 36 E % (fasting blood glucose measured prior to glucose challenge). Both casein fed groups lead to better Glucose tolerance immediately at the end of the Phase I.

Glucose Homeostasis after Phase II: A

Figure 6:
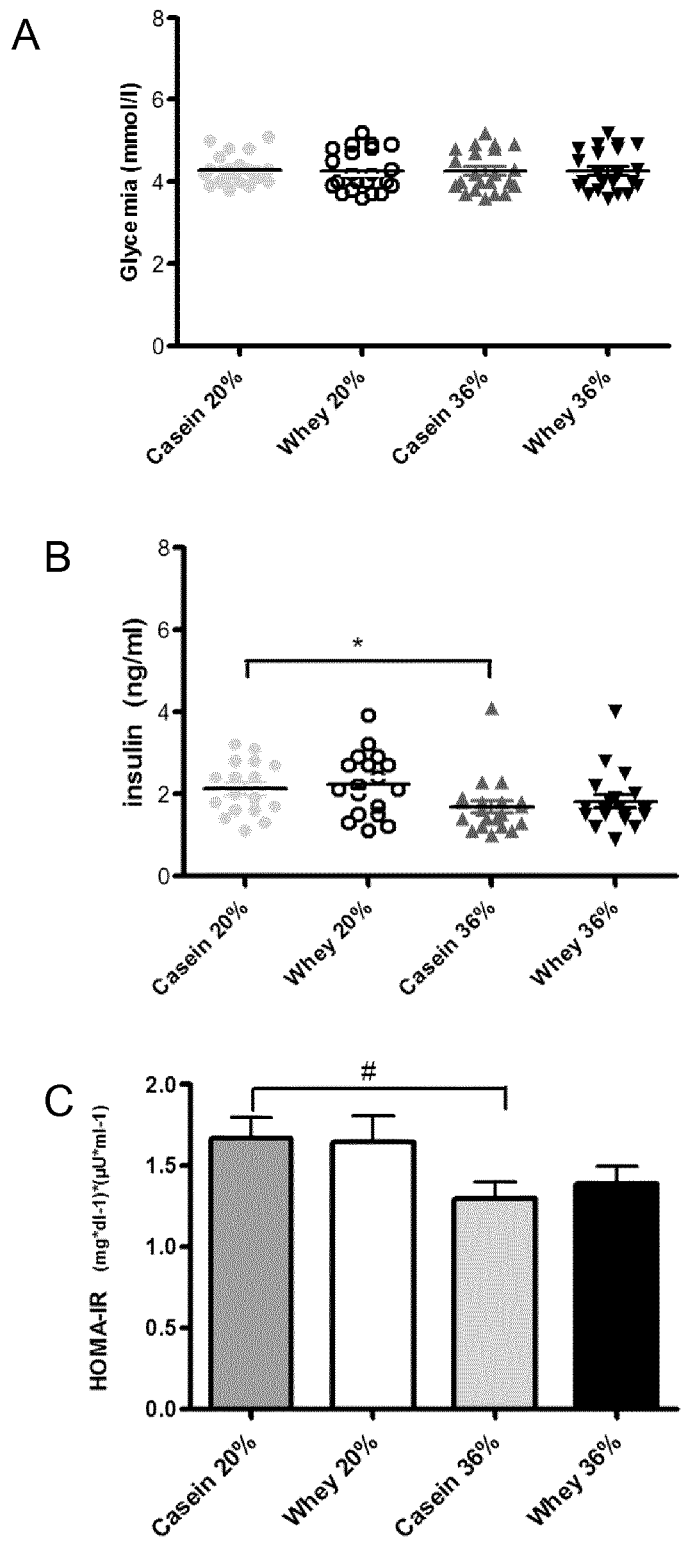
FIG. 6 shows the fasting glucose homeostasis at the end of the chow diet (ie end of Phase II:A)(165 days old). Fasting glycemia (A), Fasting insulinemia (B), HOMA-IR (C). Results are expressed as med±SEMedian. * significant difference with P<0.05; # significant difference with P<0.01.

After 17 weeks on chow diet, fasting glycemia and insulinemia were measured and results are shown in FIG. 6. The baseline glycemia did not differ between groups, but Casein 20 E % had a higher insulin level than Casein 36 E % (23% higher, p=0.02), resulting in a higher HOMA-IR value. The overall results highlight less insulin sensitivity in Casein 20 E % than Casein 36 E % at 165 days of age.

At the end of Phase II:A, ie after eating Normal Chow diet, another oral glucose tolerance test was performed. At this point, there was no difference in baseline glycemia (FIG. 6 A). However, Casein 20 E % displayed significantly higher levels of Insulin than Casein 36 E % (FIG. 6B), and therefore indicative of less insulin sensitivity (higher HOMA-IR).

The homeostasis model assessment of insulin resistance (HOMA-IR) was described by Matthews et al. (Diabetologia 28: 412-419, 1985) as a measure of basal insulin sensitivity. HOMA-IR was calculated as the product of the FPG (fasting plasma glucose) and FPI (fasting plasma insulin) levels, divided by a constant, assuming that control young adult rats have an average HOMA-IR of 1, analogous to the assumptions applied in the development of HOMA-IR in humans (q.v.). The equation was as follows HOMA-IR=(FPG×FPI)/2430, where FPI was in microunits per milliliter and FPG in milligram per deciliter (Cacho et al, American Journal of Physiology—Endocrinology and Metabolism 2008: 295. E1269-E1276)

Glucose Homeostasis after Phase II: B

An oral glucose tolerance test was also performed at age of 287 days, after 5 weeks on high fat diet, and results are represented in FIG. 7.

Whey 36 E % had both a significant higher baseline glycemia and insulinemia than Casein 36 E % (p<0.05) and also higher insulinemia than Whey 20 E % (p<0.05). After a glucose challenge, the insulin response curve showed that Casein 20 E % had a higher Cmax insulin value than Casein 36 E % (p<0.01) and also a higher AUC insulin (p<0.05).

An increase in both basal plasma glucose and insulin levels, indicates that whey 36 E % had an impaired fasting glucose and a basal insulin resistance.

Also an increase in AUC insulin in Casein 20 E % vs Casein 36 E % is also an indicator of IR.

Index of Insulin Sensitivity.

The index of insulin sensitivity (HOMA-IR) throughout the study is presented in FIG. 8. During the experimental diet period, no difference was observed in HOMA-IR among all groups (FIG. 8A). Later at age of 165 days (during low fat chow diet), Casein 20 E % had a higher HOMA-IR than Casein 36 E % (p<0.01) suggesting lower insulin sensitivity but this difference was no longer evident later on. At the end of the high fat period (age 287 days), Whey 36 E % exhibited the highest HOMA-IR value suggesting a decrease in insulin sensitivity in adult life under obesogenic environment (FIG. 8C).

No difference in HOMA-IR was found during Phase I. After Phase II:A Casein 20 E % had significantly higher HOMA-IR Index than Casein 36 E %, but the others were not significantly different. However, at end of Phase II: B (after challenge with high fat diet) Whey 36 E % had significantly higher HOMA-IR than both casein 36 E %.

REFERENCES

1. Barker D J et al Horm Res 42, 223-230. 1994.
2. Lucas A. CIBA Foundation Symposium 156. Whiley, Chichester, UK. 38-55. 1991.
3. Lucas A et al. BMJ 319, 245-249. 2012.
4. Barker et Lancet, 938-941. 1993.
5. Lanigan J et al Proc Nutr Soc. 68, 422-429. 2009.
6. Hales C N et al. BMJ 303, 1019-1022. 1991.
7. McCance. BMJ 308, 942-945. 1994.
8. Okosun et al, Int J Obes. Related Matab Disord 24, 479-484. 2000.
9. Perrie F. O'Tierney et al. The journal of Nutrition 139, 422-425. 2009.
10. Owen C G et al. Pediatrics 115, 1367-1377. 2005.
11. Harder The et al. Am J Epidemiol. 162, 397-403. 2005.
12. K B Michels et al. International Journal of Obesity 31, 1078-1085. 2007.
13. Kramer M S et al. Am J Clin Nutr 86, 1717-1721. 2007.
14. Law C M et al. J Epidemiol Community Health 46, 184-188. 1992.
15. Eriksson J G et al. Diabetes Care 26, 3006-3010. 2003.
16. Forsen T J et al. Ann Med. 2004; 36:389-92. Ann Med. 2004.
17. Berthold et al. The American Journal of Clinical Nutrition 89, 1836-1845. 2009.

The invention claimed is:

1. A method for reducing the risk of a metabolic syndrome disorder appearing later in life, the method comprising administering a nutritional composition that comprises at least 95 weight % casein based on the total protein content of the nutritional composition to an infant whose birth weight was normal or above normal, the nutritional composition further comprises a carbohydrate source, a lipid source, vitamins and minerals, the nutritional composition comprises 2.0 g protein/100 kcal to 5 g protein/100 kcal, wherein at least a portion of the casein is intact protein, wherein the nutritional composition is administered to the infant at least once per day for a time period that is from birth to 36 months of age.

2. The method according to claim 1, wherein the nutritional composition comprises 2.0 g protein/100 kcal to 2.2 g protein/100 kcal.

3. The method according to claim 1 wherein the nutritional composition comprises at least 99 weight % casein based on the total protein content of the nutritional composition.

4. The method according to claim 1 wherein the nutritional composition comprises 100 weight % casein based on the total protein content of the nutritional composition.

5. The method according to claim 1 wherein the disorder is selected from the group consisting of diabetes mellitus, impaired glucose tolerance, impaired fasting glucose, insulin resistance, hypertension, dyslipidemia, overweight, obesity and microalbuminuria.

6. The method according to claim 1 wherein the casein in the nutritional composition is bovine.

7. The method according to claim 1, wherein the birth weight of the infant was normal.

8. The method according to claim 1, wherein the birth weight of the infant was above normal.

9. The method according to claim 1, wherein the infant was born to a mother who herself suffered or suffers from one or more metabolic syndrome disorders or from gestational diabetes.

10. The method according to claim 1, wherein the nutritional composition is administered to the infant during the weaning period.

11. The method according to claim 1 wherein the method is reducing the risk of a metabolic syndrome disorder later in life when exposed to an adipogenic diet.

12. The method according to claim 1 wherein the nutritional composition is a medical food.

13. The method according to claim 1 wherein the nutritional composition is an infant formula.

14. The method according to claim 1 wherein the infant has not undergone a period of catch-up growth following a period of growth restriction.

15. The method according to claim 1 wherein the infant had a non-restricted food intake and normal growth during infancy.

* * * * *